US008338186B2

(12) United States Patent
Hollebone et al.

(10) Patent No.: US 8,338,186 B2
(45) Date of Patent: Dec. 25, 2012

(54) METHOD AND SYSTEM FOR FLUID PURIFICATION AND ANALYSIS

(75) Inventors: Bryan R. Hollebone, Ottawa (CA); Kexing Liu, Nepean (CA); Michael Allan Donkers, Ottawa (CA)

(73) Assignee: Ecovu Analytics Inc., Ottawa (CA)

( * ) Notice: Subject to any disclaimer, the term of this patent is extended or adjusted under 35 U.S.C. 154(b) by 241 days.

(21) Appl. No.: 12/790,924

(22) Filed: May 31, 2010

(65) Prior Publication Data

US 2010/0237018 A1    Sep. 23, 2010

Related U.S. Application Data

(63) Continuation-in-part of application No. 11/435,720, filed on May 18, 2006, now Pat. No. 7,727,772.

(60) Provisional application No. 60/681,714, filed on May 18, 2005.

(51) Int. Cl.
*G01N 21/03* (2006.01)
*G01N 21/00* (2006.01)
*G01N 31/00* (2006.01)
*G01N 33/00* (2006.01)

(52) U.S. Cl. .......................................... 436/165; 422/62
(58) Field of Classification Search .................... 436/165
See application file for complete search history.

(56) References Cited

U.S. PATENT DOCUMENTS

| | | | |
|---|---|---|---|
| 3,946,239 A | 3/1976 | Salzman | |
| 4,076,420 A | 2/1978 | De Maeyer | |
| 4,188,543 A | 2/1980 | Brunsting | |
| 4,200,802 A | 4/1980 | Salzman | |
| 4,245,910 A | 1/1981 | Kallander | |
| 4,304,996 A | 12/1981 | Blades | |
| 4,557,603 A | 12/1985 | Oehler | |
| 4,808,825 A | 2/1989 | Miyatake | |

(Continued)

FOREIGN PATENT DOCUMENTS

CA        2504703        10/1994

(Continued)

OTHER PUBLICATIONS

Pickering, John et al. "Double-integraing-shere system for measuring the optical properties of tissue", Applied Optics, vol. 32, No. 4, p. 399-410, Feb. 1, 1993.

(Continued)

*Primary Examiner* — Sam P Siefke
*Assistant Examiner* — Bryan Kilpatrick
(74) *Attorney, Agent, or Firm* — IP-MEX Inc.; Victoria Donnelly

(57) ABSTRACT

A system and method for purifying an aqueous contaminated fluid from colloidal contaminants using a closed-loop feedback control system are disclosed. Contaminated fluid flows into a mixer and mixed with a purifying agent, such as diatomaceous earth, to facilitate metathesis reaction between the purifying agent and the contaminants. The purifying agent entraps the contaminants, and is subsequently removed in a separator into sediments. An estimation of the amount of the purifying agent to dispense is performed using pre-defined equations or look-up tables stored in the database, including relationship between the concentration of contaminants in the fluid and the concentration of the added purifying agent. An automated feedback control is applied to fine tune the purification process into compliance with regulations. High accuracy of measurements is ensured by selecting the same material for both the purifying agent and the trapping medium of analyzers, and additionally by the design of the analyzers.

20 Claims, 9 Drawing Sheets

U.S. PATENT DOCUMENTS

| | | | |
|---|---|---|---|
| 4,861,163 | A | 8/1989 | Bach |
| 5,512,491 | A | 4/1996 | Mehkeri |
| 6,563,137 | B2 | 5/2003 | Uchida |
| 6,723,554 | B1 | 4/2004 | Gaillon |
| 7,727,772 | B2 * | 6/2010 | Hollebone et al. ............ 436/165 |
| 2010/0296971 | A1 * | 11/2010 | Gaska et al. .................... 422/62 |

FOREIGN PATENT DOCUMENTS

WO     WO94/24553     10/1994

OTHER PUBLICATIONS

Gustafsson, Goran "Experiments on shock-wave focusing in an elliptical cavity", J.Appl.Phys., 61 (11), Jun. 1, 1987.

Directed light Inc. of San Jose, California USA "Cavities" at http://www.derictedlight.com/components/cavities.html, Copyright 2004.

Ball Seminconductor Inc of Allen, Texas, USA at http://ballsemi.com/NEW/BallTech/Wspherical.asp, prior to May 18, 2005.

F.V. Fifield and Peter J. Haines, "Environmental and Analytical Chemistry", Blackwell Science, 2005.

James E. Girard, "Principles of Environmental Chemistry", Jones & Bartlett Publishers, 2005.

A. Yu. Andryushchenko, A.B. Blan, S.V. Budakovsky, N.Z. Galunov, N. I. Shevtsov, O.A. Tarasenko "Scintillation material for determination of radionuclides in water" Nuclear Instruments and Methods in Physics Research A 511, 425-430, 2003.

Velicka, Vladimir "Adaptive control algorithm for time-variant processes" vol. 158, 1991.

* cited by examiner

METHOD AND SYSTEM FOR FLUID PURIFICATION AND ANALYSIS

RELATED APPLICATIONS

This application is a continuation-in-part of the U.S. patent application Ser. No. 11/435,720 filed on May 18, 2006, which has issued into a U.S. Pat. No. 7,727,772 on Jun. 1, 2010, which claims benefit of U.S. Provisional Patent Application to Hollebone et al, Ser. No. 60/681,714 filed on 18 May 2005, entire contents of both applications are incorporated herein by reference.

FIELD OF THE INVENTION

The invention relates to a method and system for fluid purification and analysis.

BACKGROUND OF THE INVENTION

It is known that water may contain impurities and contaminants, either soluble or non-soluble, e.g. in suspension, that may be harmful to human health even if present at ultra-trace levels. This concern has already given rise to numerous methods and systems of trace level water analysis. The contaminants, which are also called "analytes", in the context of trace contaminant analysis media, apparatus and procedures, e.g. heavy metals, certain organic compounds, organic microorganisms, may be present at levels of parts per billion (ppb) or trillion (ppt), or less.

In the U.S. Pat. No. 5,512,491, a trapping medium of a micro-porous absorbent material is described, which provides entrapping of colloidal and other suspended matter present in water flowing through the medium. After a sufficient amount of the suspended matter has been entrapped in the medium, ultra-trace analysis of the entrapped analytes is carried out either by optical methods, for example, photometry, fluoroscopy, spectroscopy or other methods, or by extraction.

Optical methods are usually more efficient and accurate for the trace analysis purposes. They typically require a source of excitation light for illuminating a sample containing analytes, causing it to emit a secondary light signal, e.g. transmitted, reflected, fluorescent, luminescent, scattered light or other, indicative of the presence and amount of analytes in the sample, and a detector for receiving the secondary light signal and interpreting it as a measure of fluid contamination.

Typically, the intensity of the secondary light signal is very low, as explained e.g. in the U.S. Pat. No. 4,245,910 (Kallander), where a scattered secondary light has been measured, which also varies strongly in various directions. Typically, samples containing analytes are unoriented emitters, which emit secondary light in the full $4\pi$ steradian angle. In addition, the level of the secondary light may be as low as individual photon count.

It is thus advisable to collect as much as possible of the secondary light signal at the detector to obtain a reliable contamination reading.

Such means have been known in the art. In early days, it has been suggested to use an integrating sphere for an improved light collection. However, it presents two practical problems, first, the optimum emission and detection foci are coincident at the centre of the integrating sphere, meaning the two optical intensities could not be discriminated. Secondly, the optimum positions of sample and detector are likewise coincidental.

Thus, the mechanical requirements of locating these components are mutually exclusive.

In practice, one of the two optical functions of emitting or detecting light can be removed to the outside, being replaced, e.g. by a beam entering or exiting through a small opening in the integrating sphere. However, this immediately means that the sphere is degraded to a monofunctional optical component, rather than serving as a complete optical system. A description of single and double integrating spheres is provided, e.g. in the article by John W. Pickering, Scott A. Prahl, Niek van Wieringen, Johan F. Beek, Henricus J. C. M. Sterenborg, and Martin J. C. van Gemert, "Double-integrating-sphere system for measuring the optical properties of tissue", APPLIED OPTICS, Vol. 32, No. 4, 1 Feb. (1993).

Other examples of efficient collection of light are described in the above mentioned U.S. Pat. No. 4,245,910, and also U.S. Pat. No. 4,188,543 issued to Brunsting et al.; U.S. Pat. No. 4,808,825 to Miyatake et al.; U.S. Pat. Nos. 4,200,802 and 3,946,239 to Salzman et al.; U.S. Pat. No. 4,861,163 to Bach; and U.S. Pat. No. 4,577,603 to Oehler et al. These references describe various types of reflective shells of an ellipsoidal or semi-ellipsoidal shape, which have two foci spaced from each other, and where the sample is disposed at one focal point, while the detector is placed at the other focal point to collect the secondary light emitted by the sample and reflected by the shell.

Certain other prior art applications using elliptical geometry include shock wave experiments, which focus an emission from one focus onto another focus, thereby creating a compressed liquid jet, see Gustafsson G., "Experiments on Shock-wave Focusing in an Elliptical Cavity", J. Appl. Phys. 61, 1 Jun. (1987), and elliptical flash lamp setups for pumping solid state lasers, where the two-dimensional ellipsoidal geometry is used to deliver as much of the excitation energy to the lasing media as possible, see e.g. various laser cavity products manufactured by Directed Light Inc. in San Jose, Calif., USA as described in detail at http://www.directedlight.com/components/cavities.html (2004).

It is therefore necessary to provide effective entrapping of contaminants present in the fluid to be analyzed, effective illumination of the entrapped contaminants to generate the secondary light of sufficient intensity, and to provide effective collection of the secondary light on the detector to ensure reliable measurements of the fluid contamination level.

In spite of the certain progress being made in the field of fluid contamination analysis, the need still exists in the industry for developing an improved apparatus for analyzing contaminants suspended in water or other fluids, which would be compact, portable, multi-functional, and have sufficient sensitivity for measuring trace amounts of contaminants.

In the current state of the art of water purification, water quality is controlled by measuring a value of a variable to be controlled, such as concentration of contaminants, by sampling and analyzing the contaminated water. The measured value is then compared with another pre-set value, which meets a predetermined requirement or a standard. Depending on the difference between the measured value and the pre-set value, an action is taken to adjust a dosage level of a water purification agent. So far the above procedures have been performed via human intervention, involving manual sampling of contaminated water, and remote, delayed analysis of the sampled water. Therefore they are considered "open loop" process control.

This prior art approach has many deficiencies, such as inaccurate control and delayed adjustment of the dosage level of the purifying agent, often ranging from hours to days. This can lead to fluctuations in the quality of the output water either over or under a required level. As a result, the water quality is frequently compromised.

Therefore, there is a need in the industry for the development of more advanced and accurate method and system for fluid purification, which would avoid or mitigate the drawbacks of the prior art.

SUMMARY OF THE INVENTION

It is therefore an object of the invention to provide a method and system for fluid purification and analysis, which would overcome the deficiencies of the prior art by performing the fluid analysis and purification automatically as a computer controlled process.

It is another object of the invention to provide an improved fluid contamination analyzer and a sample cell therefor.

According to one aspect of the invention, there is provided a system for purifying an aqueous contaminated fluid from colloidal contaminants using a purifying agent, the system comprising:
- (a) an input analyzer, measuring a concentration of the colloidal contaminants in the aqueous contaminated fluid, the input analyzer having a trapping medium for entrapping colloidal contaminants from the aqueous contaminated fluid flowing through the trapping medium; the trapping medium is made of the same material as the purifying agent; the purifying agent is possessing metathetical properties;
- (b) a mixer, mixing the purifying agent and the aqueous contaminated fluid, resulting in a mixture of the purifying agent with entrapped colloidal contaminants and aqueous purified fluid;
- (c) a processor and a computer readable medium having computer readable instructions stored thereon for execution by the processor, for:
    - (c1) retrieving a relationship stored in the computer readable medium between the concentration of the colloidal contaminant in the aqueous purified fluid and concentration of the purifying agent supplied to the aqueous contaminated fluid;
    - (c2) retrieving a target concentration of the colloidal contaminants in the aqueous purified fluid stored in the computer readable medium;
    - (c3) determining an estimated optimal concentration of the purifying agent in the aqueous contaminated fluid required for achieving the target concentration of the colloidal contaminants in the aqueous purified fluid based on said relationship and the target concentration;
    - (c4) controlling dispensing of the purifying agent into the mixer in an amount required to achieve the estimated optimal concentration of the purifying agent in the aqueous contaminated fluid; and
- (d) a separator, removing the purifying agent with the entrapped contaminants from the mixture to obtain the aqueous purified fluid.

The computer readable instructions (c1) for retrieving the relationship comprise coefficients of a function approximating said relationship.

The system comprises a processing unit, comprising a processor and a computer readable medium having computer readable instructions stored thereon for execution by the processor, for:
- prior to the purifying the aqueous contaminated fluid, determining the coefficients from a number of experiments, including mixing various concentrations of the purifying agent and the aqueous contaminated fluid having the predetermined type and concentration of the colloidal contaminants, and measuring a resulting concentration of the colloidal contaminants in the aqueous purified fluid, thereby obtaining said relationship.

In the system of the embodiment of the invention, the relationship is a logistic function.

In the system described above, the input analyzer comprises: a sample cell, comprising:
- (i) the trapping medium having an outer surface and an inner surface; the trapping medium being translucent and having an essentially closed form defined by the outer surface, with a cavity formed inside thereof defined by the inner surface;
- (ii) an outer structural support surface and an inner structural support surface formed on or adjacent to the outer surface and the inner surface respectively; and
- (iii) a radiation source illuminating the trapping medium with excitation radiation to cause the entrapped colloidal contaminants to generate a secondary radiation indicative of identities of the entrapped colloidal contaminants, or the identities and concentrations of the entrapped colloidal contaminants; the radiation source being placed inside the cavity to illuminate the trapping medium from inside thereof outwards.

In the system described above, the input analyzer further comprises:
- (f) a detector for detecting the secondary radiation; and
- (g) a reflective shell at least partly encompassing the sample cell and the detector, the shell having a shape defining two focal points so that radiation generated at one of the focal points is substantially reflected by the reflective shell to the other focal point, the sample cell being disposed at or in close proximity to one of the focal points, and the detector being disposed at or in close proximity to the other focal point to receive the secondary radiation generated by the entrapped colloidal contaminants.

In the system described above, the trapping medium comprises a three-dimensional matrix of micro-porous adsorbent support material, whose surface has been chemically reconstructed with a surface reconstruction reagent to bear active, hydrated hydroxyl groups, which provide irreversible binding sites, providing absorption and entrapment of colloids and entrained analytes by immobilizing said colloids on said surface through the release of hydronium/hydrogen ions from the hydroxyl groups.

The hydroxyl groups are chosen to match a range of contaminant acid constant values, $K_a$, with an appropriate range of base constant values $K_b$, and the surface reconstruction reagent comprises a metal hydroxide.

In the embodiments of the invention, said micro-porous support material comprises diatomaceous earth.

In the system described above, the computer readable instructions for controlling dispensing further comprise computer readable instructions stored in the computer readable medium for execution by the processor, for determining a rate of dispensing of the purifying agent required for continuously maintaining the estimated concentration of the purifying agent in the aqueous contaminated fluid.

The system further comprises:
- an output analyzer for measuring concentration of the colloidal contaminants in the aqueous purified fluid, the trapping medium of the output analyzer being made of the same material as the purifying agent; and
- computer readable instructions stored in the computer readable medium for execution by the processor for adjusting the rate of dispensing of the purifying agent in response to a signal from the output analyzer until the concentration of the colloidal contaminants in the aqueous purified fluid is equal to or below the target concentration.

In the embodiments of the invention, the system comprises an output analyzer for measuring concentration of the colloidal contaminants in the aqueous purified fluid, the trapping medium of the output analyzer being made of the same material as the purifying agent.

The output analyzer comprises:
(a1) a sample cell, comprising:
  (i) the trapping medium having an outer surface and an inner surface; the trapping medium being translucent and having an essentially closed form defined by the outer surface, with a cavity formed inside thereof defined by the inner surface;
  (ii) an outer structural support surface and an inner structural support surface formed on or adjacent to the outer surface and the inner surface respectively; and
  (iii) a radiation source illuminating the trapping medium with excitation radiation to cause the entrapped colloidal contaminants to generate a secondary radiation indicative of identities of the entrapped colloidal contaminants, or the identities and concentrations of the entrapped colloidal contaminants; the radiation source being placed inside the cavity to illuminate the trapping medium from inside thereof outwards.

In the embodiments of the invention, the sample cell has a substantially spherical shape, and the trapping medium comprises a concentric layer of the trapping medium.

The radiation source comprises a diffuser for dispersing the excitation radiation substantially in a $4\pi$ steradian angle.

The sample cell has a fluid inlet communicating with the trapping medium, and a fluid outlet for discharging the aqueous fluid that has passed through the trapping medium.

The sample cell comprises an outer transparent shell, which blocks the excitation radiation and passes through the secondary radiation.

The outer transparent shell further incorporates a scintillation material for detecting radioactive elements in the aqueous contaminated fluid.

The sample cell comprises an inner transparent shell disposed in the cavity and substantially surrounding the radiation source, which blocks the secondary radiation and passes through the excitation radiation.

The output analyzer further comprises:
(f) a detector for detecting the secondary radiation; and
(g) a reflective shell at least partly encompassing the sample cell and the detector, the shell having a shape defining two focal points so that radiation generated at one of the focal points is substantially reflected by the reflective shell to the other focal point, the sample cell being disposed at or in close proximity to one of the focal points, and the detector being disposed at or in close proximity to the other focal point to receive the secondary radiation generated by the entrapped colloidal contaminants.

The reflective shell has one of the following shapes: an ellipsoidal shape; a shape of a truncated ellipsoid; a hyperboloid; a truncated hyperboloid; a paraboloid; a truncated paraboloid.

In the system described above, the secondary radiation is a fluorescent radiation generated by the entrapped colloidal contaminant. The secondary radiation or lack thereof is generated in one of the following spectroscopic techniques: Magnetic Circular Dichroism (MCD); Scattering, comprising Raman scattering; Scintillation; Photo-Acoustic; Fluorescence; Phosphorescence; Luminescence; or Absorbance.

In one embodiment, input and output analyzers comprise a detector, which has two back-to-back photo-detectors, having their detecting windows facing in substantially opposite directions.

Alternatively, the detector may comprise a semiconductor ball, which is used as a detecting component in the detector.

In the system described above, the separator is one of the following: hydrocyclone, spiral separator, filter based separation system, clarifier, dissolved air flotation system, centrifuge, fluidized bed; and the mixer is one of the following: a helical static mixer, vortex mixer, mixing eductor, Jacobi-Tarbox eductor, tank eductor, propeller blade mixer, fluidized bed, ultrasonic mixer, rotary mixer, high shear mixer, tumble drum.

According to another aspect of the invention, there is provided a method of purifying an aqueous contaminated fluid from colloidal contaminants using a purifying agent, the method comprising:
  (a) measuring concentration of the colloidal contaminants in the aqueous contaminated fluid, including directing a flow of the aqueous contaminated fluid through a trapping medium made of the same material as the purifying agent; the purifying agent possessing metathetical properties;
  (a1) retrieving a relationship between the concentration of the colloidal contaminant in the aqueous purified fluid and concentration of the purifying agent aqueous purified fluid;
  (b) selecting a target concentration of the colloidal contaminants in the aqueous purified fluid;
  (c) determining an estimated optimal concentration of the purifying agent in the aqueous contaminated fluid required for achieving the target concentration of the colloidal contaminants in the aqueous purified fluid based on said relationship and the target concentration;
  (d) controlling dispensing of the purifying agent in an amount required to achieve the estimated optimal concentration of the purifying agent in the aqueous contaminated fluid;
  (e) mixing the purifying agent dispensed in the step (d) and the aqueous contaminated fluid, resulting in a mixture of the purifying agent with the entrapped colloidal contaminants and the aqueous purified fluid; and
  (f) separating the purifying agent with the entrapped contaminants from the mixture to obtain the aqueous purified fluid.

The step of retrieving the relationship comprises retrieving coefficients of a function approximating said relationship.

The method further comprises determining the coefficients, including performing a number of experiments, prior to purifying the aqueous contaminated fluid, by mixing various concentrations of the purifying agent and the aqueous contaminated fluid having the predetermined type and concentration of the colloidal contaminants, and measuring a resulting concentration of the colloidal contaminants in the aqueous purified fluid, thereby obtaining said relationship.

In the method of the embodiments of the invention, said relationship is a logistic function.

The method further comprises determining a rate of dispensing of the purifying agent required to continuously maintain the estimated concentration of the purifying agent in the aqueous contaminated fluid.

The method further comprises:
  measuring concentration of the colloidal contaminants in the aqueous purified fluid, including directing a flow of the aqueous purified fluid through a trapping medium made of the same material as the purifying agent; and adjusting the rate of dispensing of the purifying agent in response to a signal indicative of the measured concentration of the colloidal contaminants in the aqueous purified fluid until the concentration of the colloidal contaminants in the aqueous purified fluid is equal to or below the target concentration.

Thus, an improved system and method of water purification have been provided.

BRIEF DESCRIPTION OF THE DRAWINGS

The invention will be described in more detail with the reference to the attached drawings, in which.

DETAILED DESCRIPTION OF THE EMBODIMENTS OF THE INVENTION

The embodiments of the present invention overcome the deficiencies of the prior art by performing water analysis and purification automatically as a computer controlled process.

The embodiments of the present invention describe hardware components and associated methods for remotely monitoring concentration of colloidal contaminants in the contaminated water, or an input concentration, and adjusting the water purification process in compliance with water quality regulations.

Sample Cell

Figure 1:
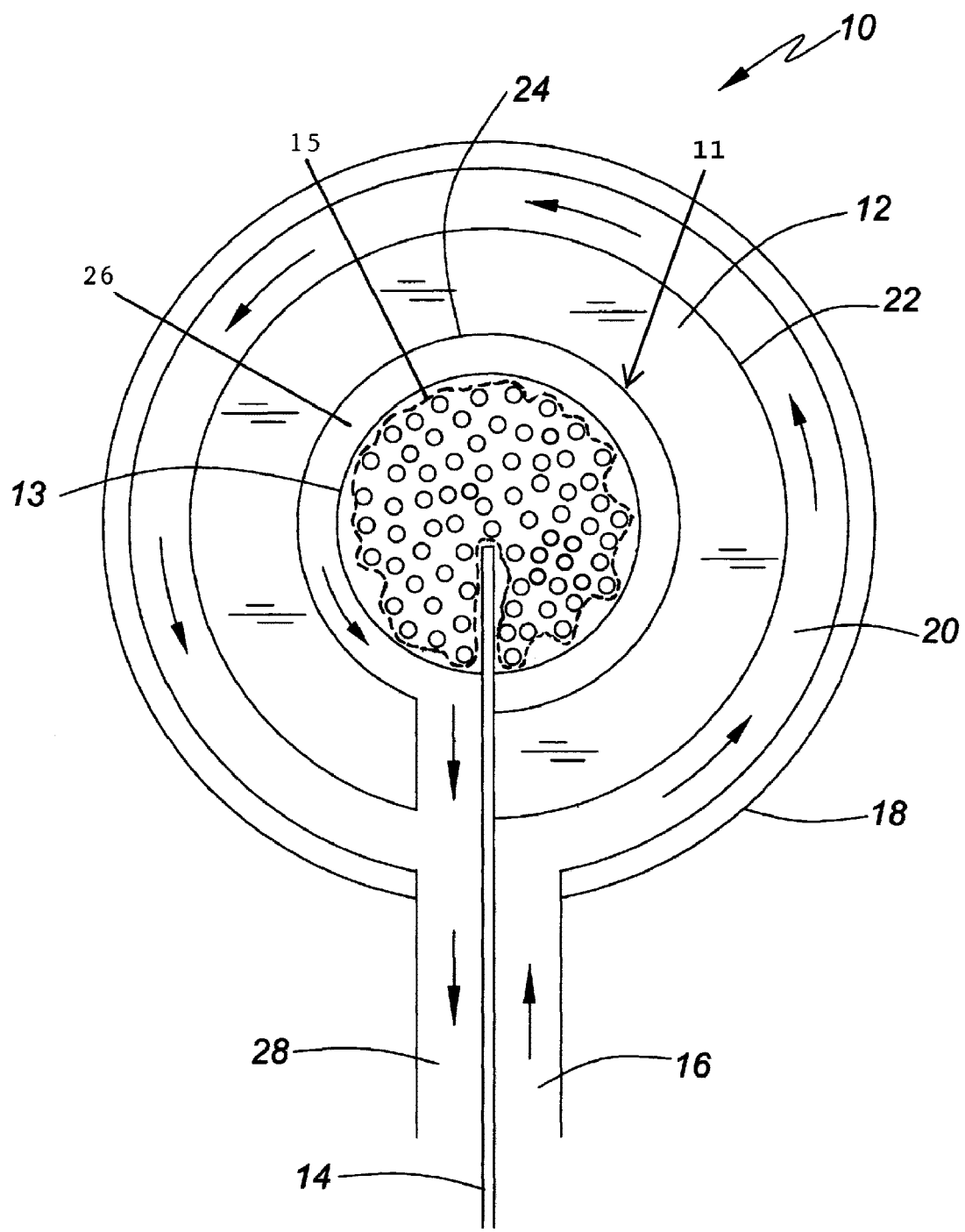
FIG. 1 is a schematic cross-sectional view of one form of a sample cell.
Figure 1A:
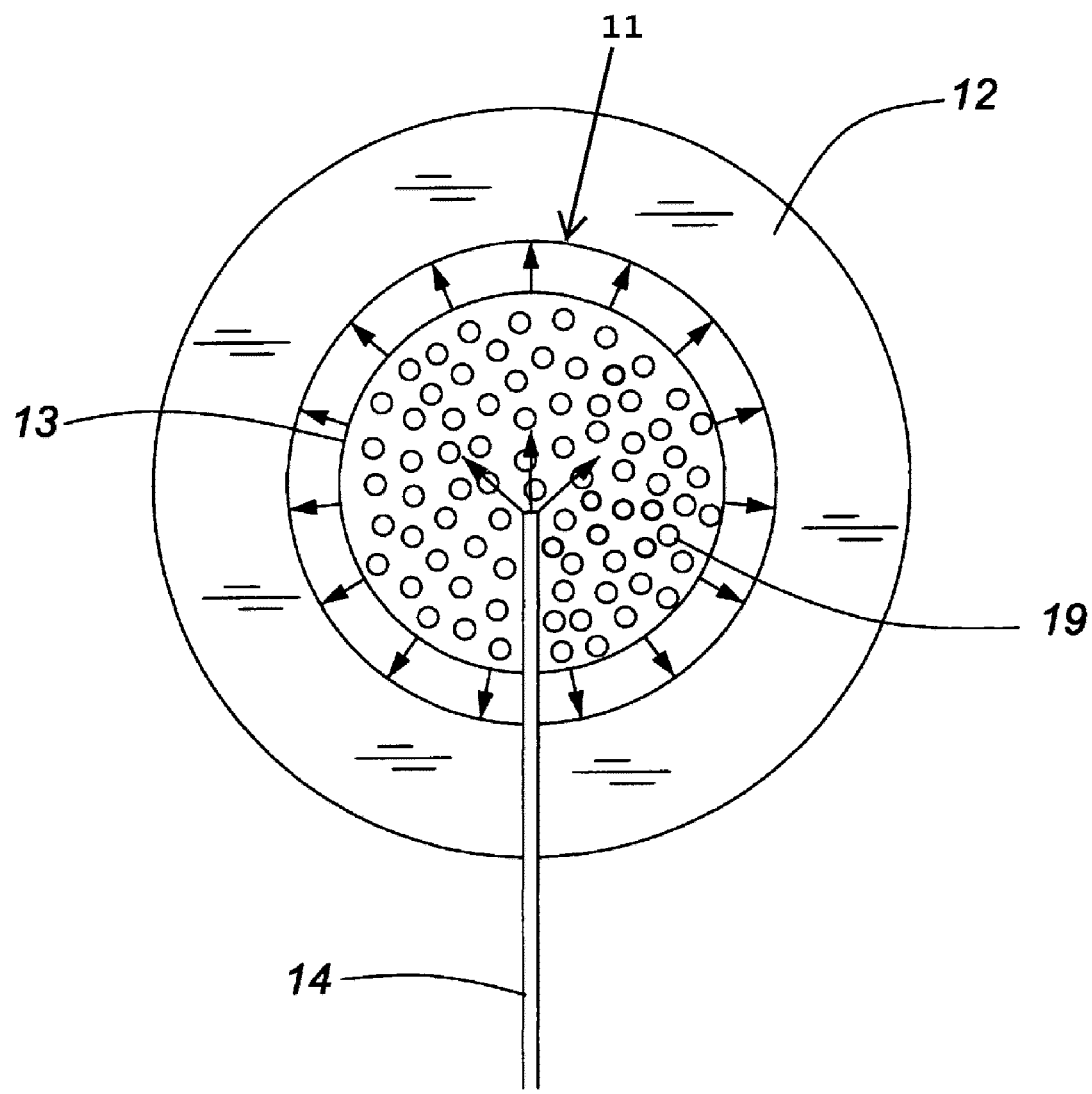
FIG. 1A shows the trapping medium and the radiation source of the sample cell of FIG. 1 in more detail.

FIG. 1 illustrates one form of a sample cell 10 for the fluid contamination analyzer of the embodiment of the present invention, the sample cell 10 being suitable for an optical fluorescent analysis of contaminants. The cell 10 has a substantially spherical shape and includes a concentric layer of the trapping medium 12 for trapping contaminants from a fluid flowing therethrough, the trapping medium having an internal cavity 11, where a radiation source (light source) 13 disposed to illuminate the trapping medium 12 from inside thereof outwards. In the embodiment of the invention, the trapping medium 12 is a gel previously patented by the Applicant and described in detail in the U.S. Pat. No. 5,512,491 to Mehkeri et al. entitled "METHOD FOR ULTRA-TRACE LEVEL ANALYSIS OF WATER" issued Apr. 30, 1996 and Canadian patent No. 2,160,235 to Mehkeri et al entitled "A SYSTEM FOR ULTRA-TRACE LEVEL ANALYSIS OF WATER AND A TRAPPING MEDIUM THEREFOR" issued Jul. 5, 2005. For further clarity, the trapping medium 12 having the internal cavity 11 and the light source 13 of FIG. 1 are also illustrated in FIG. 1A.

For convenience, a short description of the properties of the trapping medium is reproduced below.

The trapping medium may comprise a variety of micro-porous materials that present "active" hydroxyl groups over the surface of such material. "Active" hydroxyl groups are those capable of forming new bonds with the hydroxyl-bridges found within the colloidal carriers. This is effected through the release or elimination of a hydrogen ion.

Such hydroxyl groups may be formed on the surfaces of both organic and inorganic materials. An inorganic example would be a micro-porous support coated with freshly-prepared aluminum hydroxide. Suitable supports include zeolites, kieselguhr, fuller's or diatomaceous earth, alumina and silica gel. A calcined diatomaceous earth product produced by John Mansville Corporation and sold under the trade mark CELITE® is moderately directly effective in this procedure as it contains active hydroxyl groups in its natural form when hydrated and has a high internal surface area with voids that readily accommodate colloidal material. CELITE®, as with the other referenced micro-porous inorganic materials, will perform in a superior manner if specifically treated to add hydroxyl groups, which are chosen to match the range of contaminant acid constant values, Ka, with an appropriate range of base constant values Kb.

An organic example of a suitable trapping media is the range of porous materials originating from Pharmacia Incorporated of New Jersey and sold under the trade mark SEPHADEX®. This material is a polymerized polysaccharide in the form of beads. Specified pore-sizes can be prepared as required, ranging from 100 to 1 million Daltons. This material contains naturally "active" hydroxyl groups as part of the sugar structure with an appropriate range of Kb values for trapping contaminants.

Trapping media provided with the appropriate range of active hydroxyl groups have the valuable feature that the colloidal carriers become irreversibly bound in the medium. It is believed that this occurs due to a chemical reconstruction process on the surfaces of the medium, in which they become bound by an esterification reaction to the hydroxyl groups. This is suggested by the fact that it has been found that for each ion of the colloid, which is bound, a hydrogen ion is released in its typically hydrated form known as a "hydronium ion". Under electron microscopy, the immobilized colloidal gel can actually be seen accumulated within the pores of the trapping media.

It appears, therefore, that the dissociation constant for the colloidal gels, once absorbed, has been reduced by many orders of magnitude by establishing the conditions of matching Ka and Kb values to achieve complete reaction, called metathesis, compared to trapping on conventional adsorber materials such as AMBERLITE® resins.

The efficiency of the trapping of the heavy metals within trapping media can be influenced, as well, by adjusting the pH of the water sample being fed to the trapping media. The pH may be adjusted to the optimum values for effecting the precipitation, as hydroxides, of the metal, or groups of metals being isolated.

Such metathetical trapping media make possible the ultra-trace analysis of contaminants of greatest concern to society, e.g. the detection of hydrophobic organic substances and insoluble hydroxides of heavy metals. Examples include polychlorinated biphenyls (PCB's), dioxins, furans, polycyclic aromatic hydrocarbons (PAH's), lead, chromium, cadmium, mercury, etc. The metathetical trapping media may also be capable to accumulate and concentrate bacterial, protozoa, diatoms and other microbiota.

Referring back to FIGS. 1 and 1A, the light source 13 is formed within the internal cavity 11 of the trapping medium 12. The light source 13 has a diffuser 15, comprising a plurality of dispersing elements 19, e.g. in the form of small glass or plastic balls (beads) or similar objects, which scatter light in various directions, and an optical fiber 14 supplying the excitation light at the excitation line of the fluorescence for the analyte of interest to illuminate the dispersion elements 19. The optical fiber 14 illuminates the diffuser 15 approximately at the centre thereof, causing the dispersion elements 19 to scatter the excitation light in substantially $4\pi$ steradian and illuminate the trapping medium 12 substantially isotropically.

Other components of the sample cell 10 are as follows:

A water feed in passage 16 for supplying water to the sample cell 10, which is facilitated by a inlet tube or capillary connected to a pump;

An outer transparent shell 18, which is made of a transparent plastic or similar material, and serves as a suitable emission band pass optical filter for the excitation light;

An input water channel 20 in the form of a concentric passage, which conducts the water symmetrically around the trapping medium 12;

An outer porous surface 22, which is adjacent to or deposited on the outer surface of the trapping medium 12 and provides structural support against the influx of water from the input water channel 20 to prevent the trapping medium 12 from being washed away;

An inner perforated membrane 24, such as aluminized Mylar®, which is adjacent to or deposited on the inner surface of the trapping medium 12 and provides structural support for the trapping medium 12 so as to prevent wash through and maintain the position of the trapped trace contaminants. Preferably, the inner perforated membrane 24 is also reflective to the fluorescence line of the secondary light emitted by the contaminants entrapped in the trapping medium 12;

An output water channel 26 in the form of a concentric passage between the trapping medium 12 and the light source 13, which conducts the water symmetrically around the light source 13 and outside of the sample cell 10; and A water feed output passage 28 for removing water from the sample cell 10, which is facilitated through the holes in the inner perforated membrane 24 past the diffuser 15 and out through an outlet tube or capillary. Conveniently, the outlet pipe may also serve to deliver the optical fiber 14 to illuminate the diffuser 15.

In operation, the contaminated water or any other aqueous fluid to be analyzed is passed through the sample cell 10 via an inlet tube 16 and then through the trapping medium 12, which collects contaminants present in the water flowing therethrough. The water is withdrawn through an outlet tube 28. The light source 13 provides substantially isotropic illumination of the trapping medium 12 from inside outwards. When the trapping medium is illuminated by the light source 13, the contaminants entrapped in the trapping medium 12 emit secondary fluorescent light (secondary radiation), which is collected and analyzed in the fluid contamination analyzer of the embodiment of the present invention as will be described in detail below.

The water path in the sample cell 10 is as follows. The water containing the analyte of interest is pumped into the sample cell via an inlet tube or capillary 16 where it travels into the input water channel 20. Then the water travels through the outer porous surface 22 and through the trapping medium 12. The water flow then continues through the inner perforated membrane 24 to the water output channel 26 past the light source 13, and then out of the sample cell 10 through the water feed output 28.

The light path in the sample cell 10 is as follows. The excitation light is guided from a source (not shown), e.g. a laser, through the optical fiber 14 into the diffuser 15. The optical fiber 14 may be separate or conveniently contained in the water feed output 28. The excitation light is scattered by the dispersion elements 19 within the diffuser 15 and then propagates through the inner perforated membrane 24 and illuminates the analyte of interest within the trapping medium 12. The optically excited analyte then emits secondary (fluorescent) light sending it substantially in all directions.

Part of this secondary fluorescent light propagates through the trapping medium 12, the water input channel 20, the outer porous surface 22, and further through the outer transparent surface 18. To facilitate propagation of the other part of the secondary fluorescent light, a reflective coating is preferably placed on the surfaces of the inner perforated membrane 24, the outer transparent surface 18 and possibly on the outer porous surface 22 should the need arise.

In general, the sample cell 10 described above satisfies the following requirements:

the trapping medium has an essentially closed form with a cavity inside the trapping medium, e.g. the trapping medium 12 may have a form of a spherical layer as described above;

the trapping medium is illuminated from inside thereof and outwards, e.g. the trapping medium is illuminated from inside the cavity 11 by the light source 13 as described above;

an excitation light source is used to excite fluorescent molecules entrapped in the trapping medium;

an optical filtering mechanism is used to filter excitation photons while being transparent to the fluorescent photons emitted from the entrapped contaminants;

the water flow around the trapping medium has to remain low enough in turbidity in order to prevent the clogging of the porous surfaces and not to obstruct light propagation;

the trapping medium is made sufficiently translucent by the surface activation reaction to allow sufficient propagation of the excitation light inside the volume to cause the excitation of the entrapped contaminants.

The spherical structure of the sample cell 10 should be amenable to disassembling for loading and removal of the trapping medium 12, the dispersing elements 19 and the optical fiber 14. To this end, the sample cell 10 may be constructed of two halves, with their division plane approximately coextensive with, or parallel to the axis of the optical fiber 14. The two halves may be assembled using waterproof seals. Alternatively, the sample cell 10 may be constructed of a number of symmetrical or asymmetrical sectors instead of the two halves, which can be removed separately, and when assembled, would form the sample cell 10 of FIG. 1.

The overall structure of the sample cell 10 has preferred dimensions in the range of a few centimeters in diameter, e.g. about 2 cm diameter. Larger dimensions of the sample cell 10 are also possible, e.g. in the range of a few decimeters or larger, provided the sample cell is to be used in a stationary fluid contamination analyzer, which does not have to be portable. In this case, the weight and dimensions of the sample cell 10 and fluid contamination analyzer are not of utmost importance.

The sample cell 10 may also be altered to incorporate a scintillating material in the outer transparent shell 18. This would allow for the detection of radioactive elements in fluids by observing the radiation emitted through an interaction with the radiation produced by the decay of the analyte and the scintillator.

Another Form of Sample Cell

Figure 2:
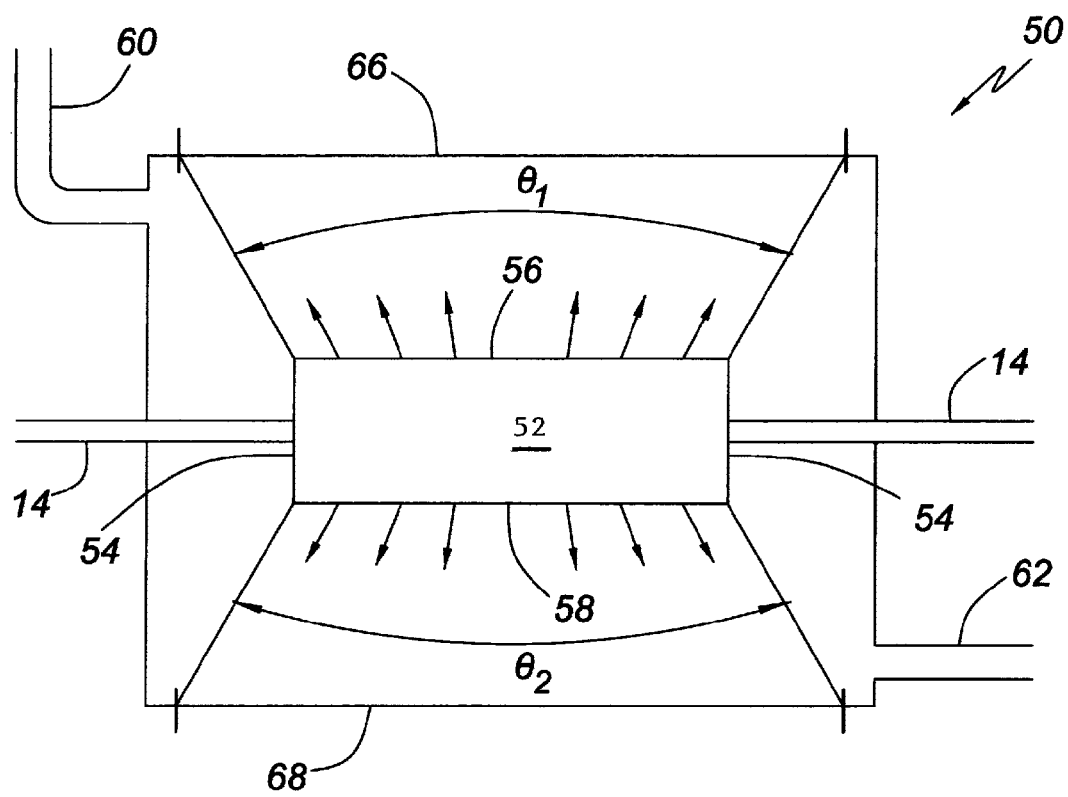
FIG. 2 is a schematic cross-sectional view of another form of the sample cell.

FIG. 2 illustrates another form of the sample cell 50 for the fluid contamination analyzer of the embodiment of the present invention. The sample cell 50 has a substantially planar geometry and holds a disk-shaped trapping medium 52 (mounting means are omitted for simplicity), having a side surface 54 and top and bottom surfaces 56 and 58 respectively. A fluid is supplied into the sample cell 50 through a fluid inlet 60, enters the trapping medium 52 through its top surface 56, flows through the trapping medium 52, and exits the trapping medium through its bottom surface 58, being removed from the sample cell 50 via fluid outlet 62. The light source is implemented in the form of at least one or more optical fibers 14, which illuminate the side surface 54 of the trapping medium 52 with the excitation light, the optical fibers being arranged preferably symmetrically so as to illuminate the side surface 54 substantially uniformly. The secondary fluorescent radiation indicative of the presence and concentration of fluid contaminants present in the fluid is stimulated by the excitation light and radiated through the top and bottom surfaces 56 and 58 of the trapping medium 52, and through respective top and bottom windows 66 and 68 of the sample cell 50. Thus, in the sample cell 50, the secondary fluorescent radiation is emitted substantially into a $2\pi$ steradian angle $\theta_1$ through the top surface 56 of the trapping medium 50, and substantially into a complementary $2\pi$ steradian angle $\theta_2$ through the bottom surface 58 of the trapping medium 50.

It is contemplated that various modifications are possible to the design of the sample cell 50. The sample cell 50 may comprise more than one disk-shaped trapping medium 52, the trapping medium 52 itself may have a different shape, e.g. slab like or other, the orientation of the trapping medium 52 within the sample cell and the respective fluid flow through the trapping medium 12 may be changed, e.g. the trapping medium 52 may be rotated at an angle, e.g. at approximately 90 degrees, compared to its current position shown in FIG. 2. Illumination of the trapping medium 52 may be performed differently, e.g. the primary radiation may illuminate one of the top or bottom surfaces 56 or 58 of the medium 52, or, alternatively, both top and bottom surfaces 56 and 58. The form of the light source may be also different as long as it supplies sufficient energy to illuminate the trapping medium 52 at the excitation line of the analyte of interest to generate enough secondary fluorescent radiation for detection purposes.

Thus, improved sample cells 10 and 50 for fluid contamination analysis have been provided.

Fluid Contamination Analyzer

Figure 3:
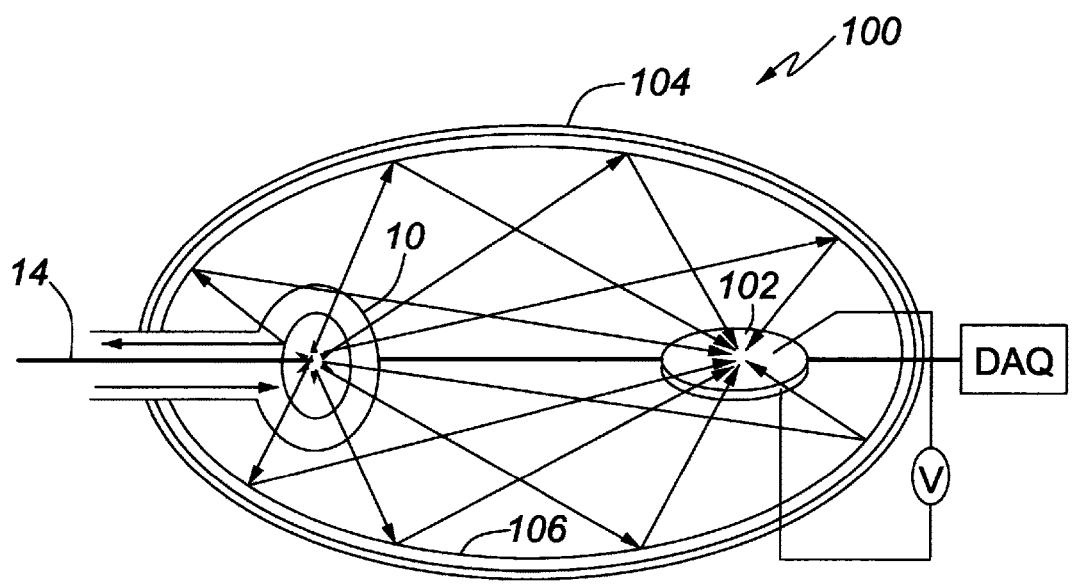
FIG. 3 shows a schematic cross-sectional view of an exemplary fluid contamination analyzer according to the embodiment of the invention.

FIG. 3 illustrates the fluid contamination analyzer 100 of the embodiment of the present invention. The fluid contamination analyzer 100 comprises the sample cell 10 described above, a detector 102 for detecting the secondary radiation; and a reflective shell 104 in the form of an ellipsoid, at least partly encompassing the sample cell 10 and the detector 102, the reflective shell 104 defining two focal points so that radiation generated at one of the focal points is reflected by the reflective shell to the other focal point, wherein the sample cell 10 is disposed at or in close proximity to one of the focal points, and the detector 102 is disposed at or in close proximity to the other focal point to receive the secondary fluorescent radiation generated by the entrapped contaminant.

The reflective shell 104 is preferably made of aluminum metal and has an internal reflective surface 106 made of gold or another suitable reflective material.

The shape of the reflective shell can be different, for example, non-continuous in the form, e.g. of a truncated ellipsoid, or resembling a hyperboloid or paraboloid as long as it serves the purpose of focusing the secondary fluorescent light emitted from the sample cell 10 onto the detector 102, which is spaced from the sample cell 10.

Figure 4:
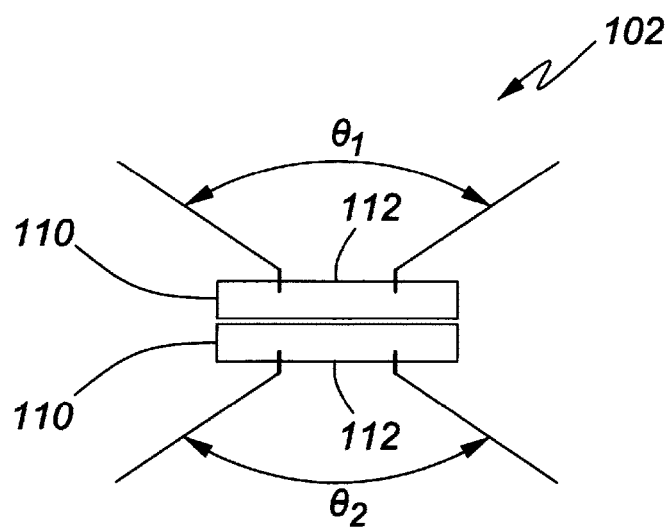
FIG. 4 illustrates one form of a detector for use in the fluid contamination analyzer of FIG. 3.

One form of the detector 102 is illustrated in FIG. 4. It comprises two back-to-back silicon photo avalanche diodes 110, with their detecting windows 112 facing in opposite directions and capable of collecting light from substantially complementary $2\pi$ steradian angles $\theta_1$ and $\theta_2$ as illustrated in FIG. 4. Accordingly this form of the detector 102 will be referred to as a "$2\pi$ detector".

Another form of the detector 102 includes an optimized solid state device as its detecting component, which has a spherical shape and is preferably made of silicon. It is operated via radio frequency or hard wired to the detector. Currently, a prototype for such solid state device is available from Ball Semiconductor Inc. of Allen, Tex., USA, which manufactures small spherical chips of about 1 mm in size.

Preferred Requirements for the Fluid Contamination Analyzer 100:

(1) The dimensions for the reflective shell are preferably of the order of 1 foot to 2 foot length by one foot in diameter (or smaller). These dimensions will be optimized for light capturing efficiency depending on the dimensions of the sample cell 10 and the detector 102, however they illustrate that the fluid contamination analyzer is intended to be portable;

(2) As mentioned previously, the turbidity of the fluid in the sample cell 10 should be kept low enough to prevent fouling of the flow apparatus. This will be characterized by the size of the porous surfaces and flow rate;

(3) There is also a possible requirement of in an inert atmosphere, e.g. nitrogen as certain flat chip detectors may have to be operated in such an environment due to manufacturer's specifications. This may also help hinder the growth of oxides on the coatings found on the optics or internal reflective surface 106. If this is necessary, then vacuum seals will be employed anywhere there are joints to the outside;

(4) As discussed above, the trapping medium 12 is to be disposable and hence removable so as to make the sample cell 10 or 50 reusable; and (5) The detector, 102, itself may require an anti-reflection (AR) coating to limit the reflection of grazing angle radiation.

As mentioned above, the contaminants are usually present in water, or any other aqueous fluid, in trace amounts. Therefore, in order to accumulate the amount of the contaminant in the trapping medium 12, which would be sufficient to provide a reliable reading at the detector 102, it is understood that the volume of water may have to be passed through the cell for a required period of time.

The fluid contamination analyzer 10 can function in two modes of operation.

In a sequential mode of operation, the fluid to be analyzed is passed through the trapping medium for a predetermined period of time to allow the accumulation of the sufficient amount of the contaminant, and after that the secondary light fluorescent analysis of the entrapped contaminant is performed in the manner described above.

In a parallel mode of operation, the light source 13 is illuminating the trapping medium, and the detector 102 is detecting the secondary fluorescent light at the same time as the fluid is flowing through the trapping medium 12. This allows monitoring of the dynamics of accumulation of the contaminant in the trapping medium and, in certain occasions, to reduce the time required for the contamination analysis, e.g. when only the presence of the contaminant has to be detected.

It is understood that, in the fluid contamination analyzer 100, the sample cell 50 described above can be also used instead of the sample cell 10. Other designs of sample cells are also possible as long as they provide a dual function of entrapping contaminants present in the fluid to be analyzed, and analyzing the presence and concentration thereof by using optical methods.

Although a fluorescence optical analysis of contaminants has been used in the preferred embodiment of the invention, it is contemplated that other spectroscopic techniques, which generate the measurable presence or absence of the secondary light indicative of the identity and concentration of contaminants, can be also employed within the spirit of the present invention.

The fluid contamination analyzer 100 of the embodiment of the present invention has the following advantages.

The fluid contamination analyzer 100 would not only provide a device that is small, rugged, field-portable and in-situ tool, but will also provide an improved detection sensitivity by a minimum of two orders of magnitude compared to currently commercial available analyzers. It is suitable for environmental analysis of micro-organisms, organic and inorganic substances found in various fluids, e.g. freshwater sources.

Furthermore, the fluid contamination analyzer 100 allows a simplified installation and removal of the trapping medium 12, which enables users to conduct sampling more frequently. This will empower plant managers with the ability to manage water in a real time, i.e. in a prevention mode as opposed to the historical monitoring and remediation mode used currently.

Method and System for Water Purification

The embodiments of the present invention overcome deficiencies of the prior art by making water treatment into a completely automatic, computer controlled "closed loop" process.

Figure 6:
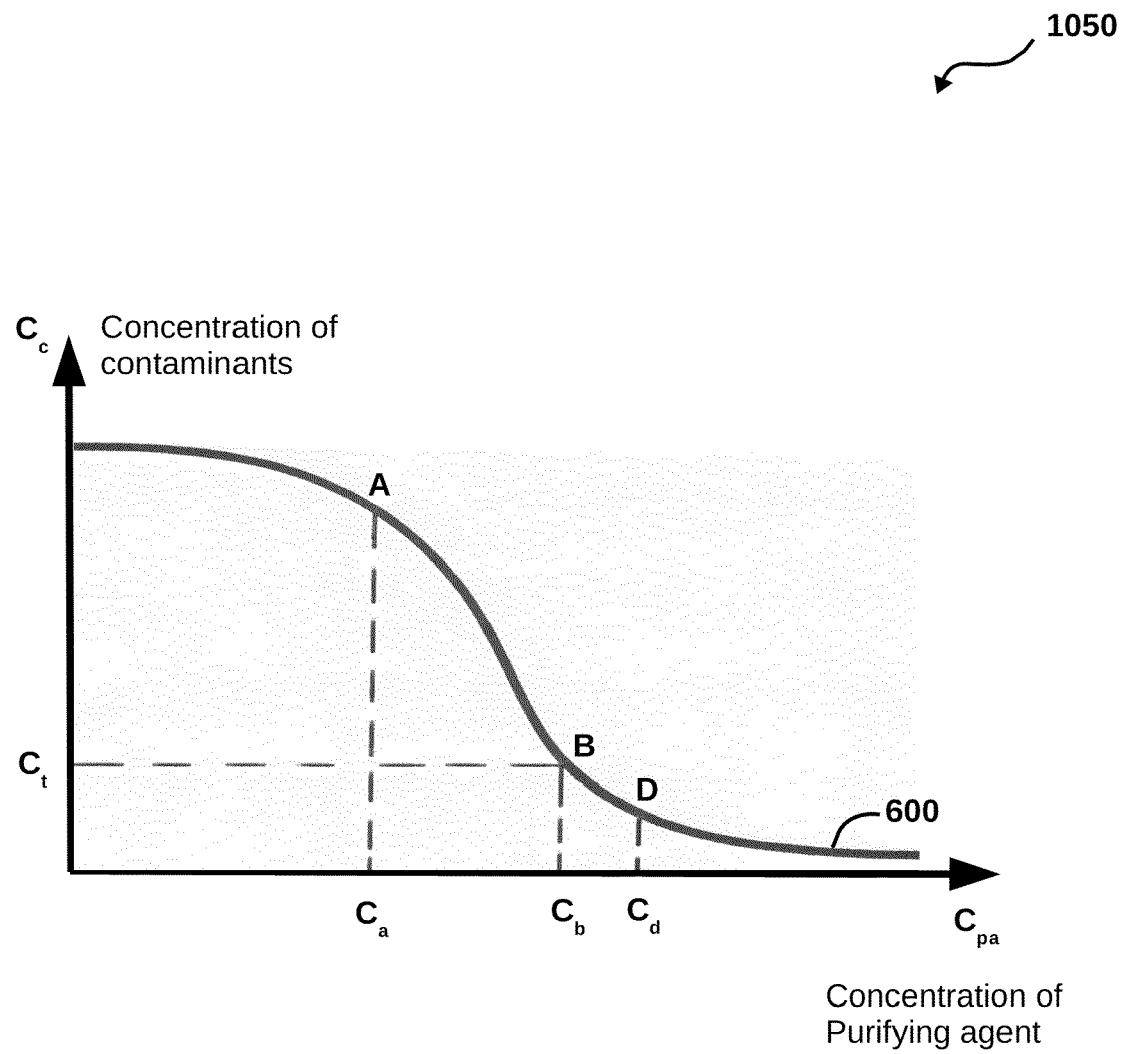
FIG. 6 shows an exemplary logistic function representing concentration of contaminants versus concentration of the purifying agent.

Water purification process employed by the embodiment of the current invention is based on mixing contaminated water with slurry of a suitable purifying agent, such as that based on diatomaceous earth or other Si source, to facilitate a metathetical reaction between the purifying agent and colloidal contaminants in the contaminated water. Since the purifying agent reacts with the colloidal contaminants in a metathetical process, the reaction proceeds until it reaches a saturation condition, the degree of purification being dependent only upon the quantity of the purifying agent employed. Typical dependence of a concentration of the colloidal contaminants in purified water, or residual concentration, upon a concentration of the purifying agent in the contaminated water is highly non-linear and is best represented by an exemplary logistic function 600 on FIG. 6, shown not to scale for clarity. A simplified form of the logistic function is often referred to as sigmoid function. The logistic function 600 has three distinct sections with boundaries between the sections conveniently represented by the points A and D. Both points A and D are the points of maximal absolute value of curvature of function 600. Concentrations of the purifying agent corresponding to the points A and D are denoted as $C_a$ and $C_d$ respectively. If the concentration of the purifying agent in the contaminated water is below $C_a$, the decrease in the concentration of the contaminants is, for all practical purposes, negligibly small. As the concentration of the purifying agent approaches $C_d$, concentration of the contaminants drops rapidly, typically through several orders of magnitude. However, increasing the concentration of the purifying agent beyond $C_d$ results in a disproportionately slow decrease in the concentration of the colloidal contaminants. Typically, a target concentration $C_t$ of contaminants in the purified water, established by regulatory authorities, falls within the interval [$C_a$, $C_d$] and is represented on FIG. 6 by an exemplary point B. Effective purification of the contaminated water is achievable if concentration of the purifying agent falls within the interval [$C_a$, $C_d$], and the regulatory requirements on the target concentration are satisfied if concentration of the purifying agent is equal or slightly below $C_t$. The concentration of the purifying agent corresponding to the point B is denoted as $C_b$ and is referred to as an optimal concentration. An amount of the purifying agent required to reach the optimal concentration is referred to as the optimal amount. For example, for water contaminated with iron at a concentration of contaminants in the contaminated water, or an input concentration, of 5 mg/L or 5 ppm, a concentration of 50 mg/L or 50 ppm of a particular purifying agent would be used to bring the target concentration to below 0.01 mg/L or 0.01 ppm.

Highly non-linear dynamics of the water purification process represented by the logistic function 600 poses significant problems in terms of practical implementation of the purification system. Indeed, $C_a$ and $C_d$ depend on the concentration of the contaminants in the contaminated water, or the input concentration, which in raw water sources can range over many orders of magnitude, typically from parts per billion to parts per thousand. To complicate the situation further, $C_a$ and $C_d$ also depend upon the choice of the purifying agent and the type of contaminants or their combinations. Typically, the interval [$C_a$, $C_d$] is narrow (shown on FIG. 6 not to scale for clarity), and therefore determining the optimal amount, or an optimal concentration, of the purifying agent $C_b$ for given conditions, which would fall into said interval and is required for effective purification to achieve the target concentration $C_t$ of contaminants in the purified water, is challenging. However, dispensing a lesser amount of the purifying agent than the optimal would mean incomplete purification, whereas dispensing too much would result mainly in the increased cost of the purifying process with disproportionately little gain in terms of the water purification.

Both disadvantages are addressed in the embodiment of the present invention by implementing a precise automatic control over dispensing the optimal amount of the purifying agent based on accurate measurements of the concentration of contaminants in the contaminated water by an analyzer, including the analyzer of the embodiments of the invention, and a particular choice of the purifying agent for the purification process, and a trapping medium for the analyzer.

In the preferred embodiment of the present invention, a high accuracy of the concentration measurements is achieved by ensuring that the contaminant capture properties of the purifying agent are exactly the same as those of the trapping medium of the analyzer. This is done by selecting the same material for the purifying agent as the material of the trapping medium of the analyzer, and by chemically treating the purifying agent in exactly the same way as the trapping medium of the analyzer. For brevity, the term "purifying agent" will further refer to the purifying agent satisfying both conditions indicated above. This ensures that contaminants relevant to the purification process are detected with the same high capture efficiency as they are removed from the raw water for all colloidal contaminants.

In the preferred embodiment of the invention, the material for both the trapping medium of the analyzer and the purifying agent are chosen to be diatomaceous earth chemically treated as described in detail in earlier U.S. Pat. No. 5,512,491 and Canadian Patent No. 2093676 to the same applicant, both patents are being incorporated here by reference. The metathetical nature of the reaction with contaminants ensures that the optimal amount of purification agent is accurately defined by the concentration perceived by the analysis.

Since the trapping medium of the analyzer specifically reacts with colloidal contaminants, the detection system has no sensitivity towards completely dissolved materials in the raw water. Therefore, untrapped contaminants will not be detected by the analyzer.

Batch Processing of Contaminated Water

Figure 5:
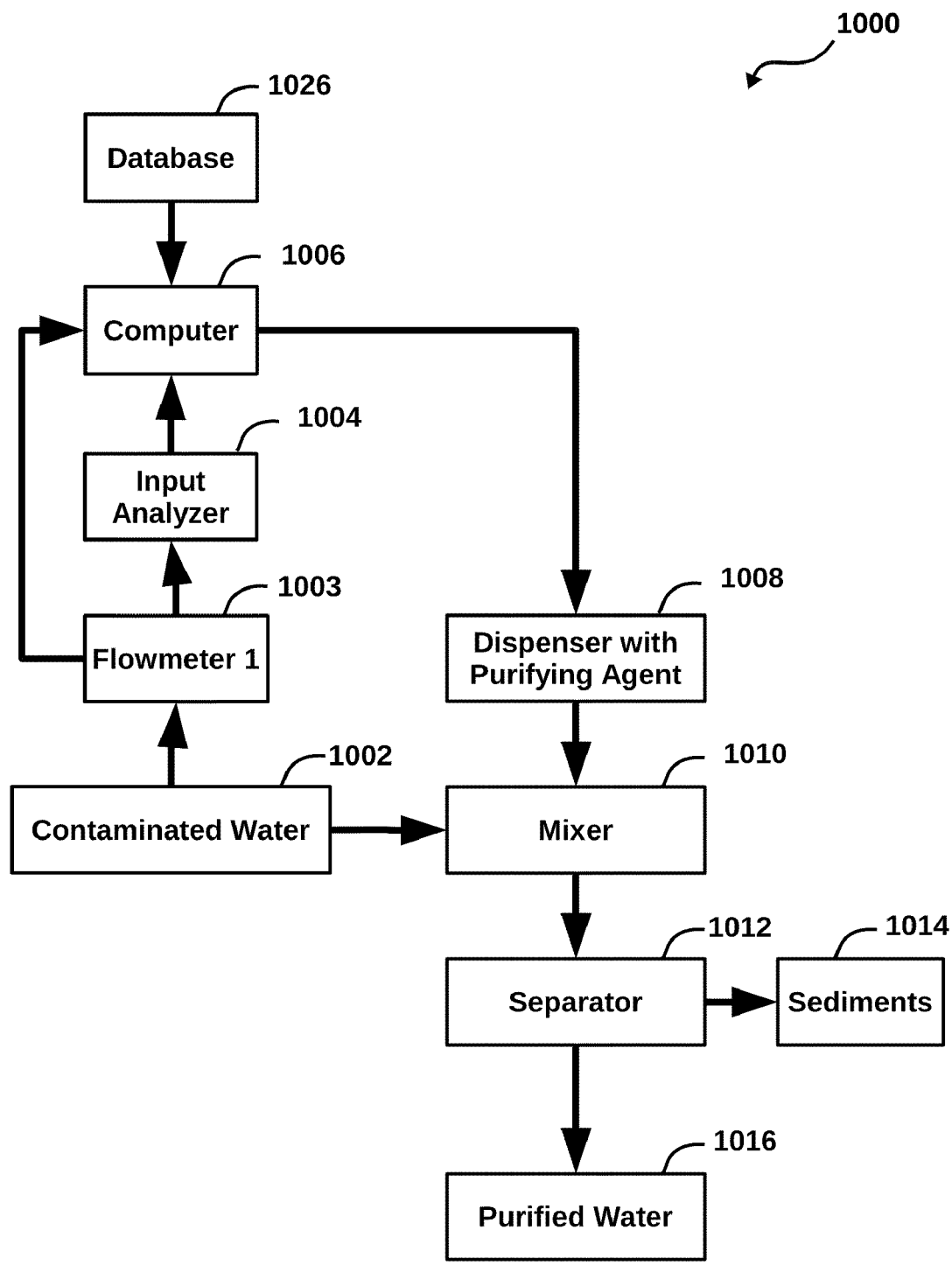
FIG. 5 illustrates a block diagram of the water purification system of an embodiment of the invention suitable for batch processing of contaminated water.

FIG. 5 illustrates an embodiment of the invention for water purification system 1000 suitable for batch processing of the contaminated water, which utilizes the water purification process described above.

A relationship between the concentration of the colloidal contaminants in the purified water $C_c$ and the concentration of the purifying agent $C_{pa}$ can be approximated by various functions, such as logistic function, polynomial function, sigmoid function etc.

In the embodiments of the invention, a relationship between the concentration of the colloidal contaminants in the purified water $C_c$ and the concentration of the purifying agent $C_{pa}$ is represented by the logistic function, such as shown on FIG. 6, which is expressed mathematically as $$C_c = a \cdot \frac{1 + b \cdot e^{-h(C_{pa}-d)}}{1 + f \cdot e^{-h(C_{pa}-d)}} \quad (1)$$

The coefficients a, b, h, d, and f depend upon the type and concentration of the colloidal contaminant or a combination of the colloidal contaminants present in the contaminated water, and the type of the purifying agent selected for the contaminated water purification.

During purification of contaminated water 1002, concentration of the colloidal contaminants is measured under control of the computer 1006 by using the flowmeter 1003 and the input analyzer 1004. In the embodiment of the invention, the input analyzer 1004 is the fluid contamination analyzer described above, and the flowmeter 1003 is a Paddlewheel Flowmeter, such as commercially available from the Cole-Parmer Instrument Company. Computer 1006, having a processor a computer readable storage medium, for example memory, DVD, CD-ROM or other storage medium, receives measurement signals from both the analyzer 1004 and the flowmeter 1003, divides the amount of the colloidal contaminants, as measured by the input analyzer 1004, by the total volume of water from which it was extracted, as determined from the flow rate measured by the flowmeter 1003, getting as a result the concentration of the colloidal contaminants in the contaminated water. This allows achieving an on-the-fly remote monitoring of the concentration of the colloidal contaminants, which is both efficient and reliable.

Provided the type of the contaminant or a combination of the contaminants in the contaminated water are known, and the concentration of the colloidal contaminants is determined as described above, the computer 1006 queries the database 1026 to retrieve coefficients a, b, h, d, and f that fully determine the logistic function (1) corresponding to the current combination of contaminants. Given the target concentration Ct, the computer 1006 computes from the fully determined logistic function an estimated optimal concentration of the purifying agent. The estimated optimal amount of the purifying agent is determined by multiplying the estimated optimal concentration of the purifying agent and the pre-determined volume of water to purify. The database 1026 comprises a computer readable storage medium having data and instructions stored thereon for execution by a processor.

For example, the following exemplary query can be sent to the database 1026:
- type of the contaminant->Arsenic;
- concentration of the contaminant in the contaminated water ->5 mg/l;
- target concentration of the contaminant in purified water ->0.01 mg/L, or 10 ppb;
- volume of treated water->1 m$^3$.

Based on the selected purifying agent, the database will search for the coefficients of the logistic function for arsenic and compute, from the fully determined logistic function, the estimated optimal amount of the purifying agent, for example 50 g.

Under control of the computer 1006, the pre-determined volume of water is pumped into the mixer 1010. Simultaneously, the estimated optimal amount of the purifying agent 1008 is dispensed into the mixer. The mixer is to provide thorough mixing between purifying agent and the contaminated water in order to reduce the diffusion time of the purifying agent in the water. In the preferred embodiment of the present invention, the mixer 1010 is a propeller blade mixer, such as one of the mixers commercially available from Sonic Corporation. The mixing time varies with the pre-determined volume of water, a type of the purifying agent used, the type and concentration of the colloidal contaminants. Typically, it is determined as 3 times the half life of the diffusing time, which in practice often translates into anywhere between a few minutes to tens of minutes. In the mixer, the colloidal contaminants are entrapped by the purifying agent forming a mixture of the purifying agent with the entrapped colloidal contaminants and purified water. The mixture is pumped into the separator 1012 to remove the entrapped colloidal contaminants by simply removing the purifying agent as sediments 1014 out of the water. Separation of the purifying agent with the entrapped contaminants from water takes up to 24 hours to complete by using the gravitational settlement process. The resulting sediment is extensively dehydrated by the chemical reaction during purification, and it represents the dry weight of initial contaminant bound to the saturation weight of the purifying agent. Since initial contaminant weight was dispersed at part per million levels, this output weight, at a density greater than water will typically be 10$^{-5}$ of the weight of treated water. Since the capture reaction is metathetical, the purifying agent is converted by chemical bonding with the contaminant to the new sediment form. It is not readily regenerated but its inert, non-toxic properties allow it to be used in several possible revenue streams. These include soil amendments if the initial waste was organic material or artificial ores if it was heavy metals. The purified water 1016 is deemed to be ready for consumption.

It is contemplated that routinely a single cycle of purification would be sufficient for achieving the target concentration due to a high accuracy of estimation of the optimal amount of the purifying agent. If the concentration of the colloidal contaminants in the purified water is higher than the target concentration, then the water is redirected back to the contaminated water 1002 for reprocessing.

Figure 5A:
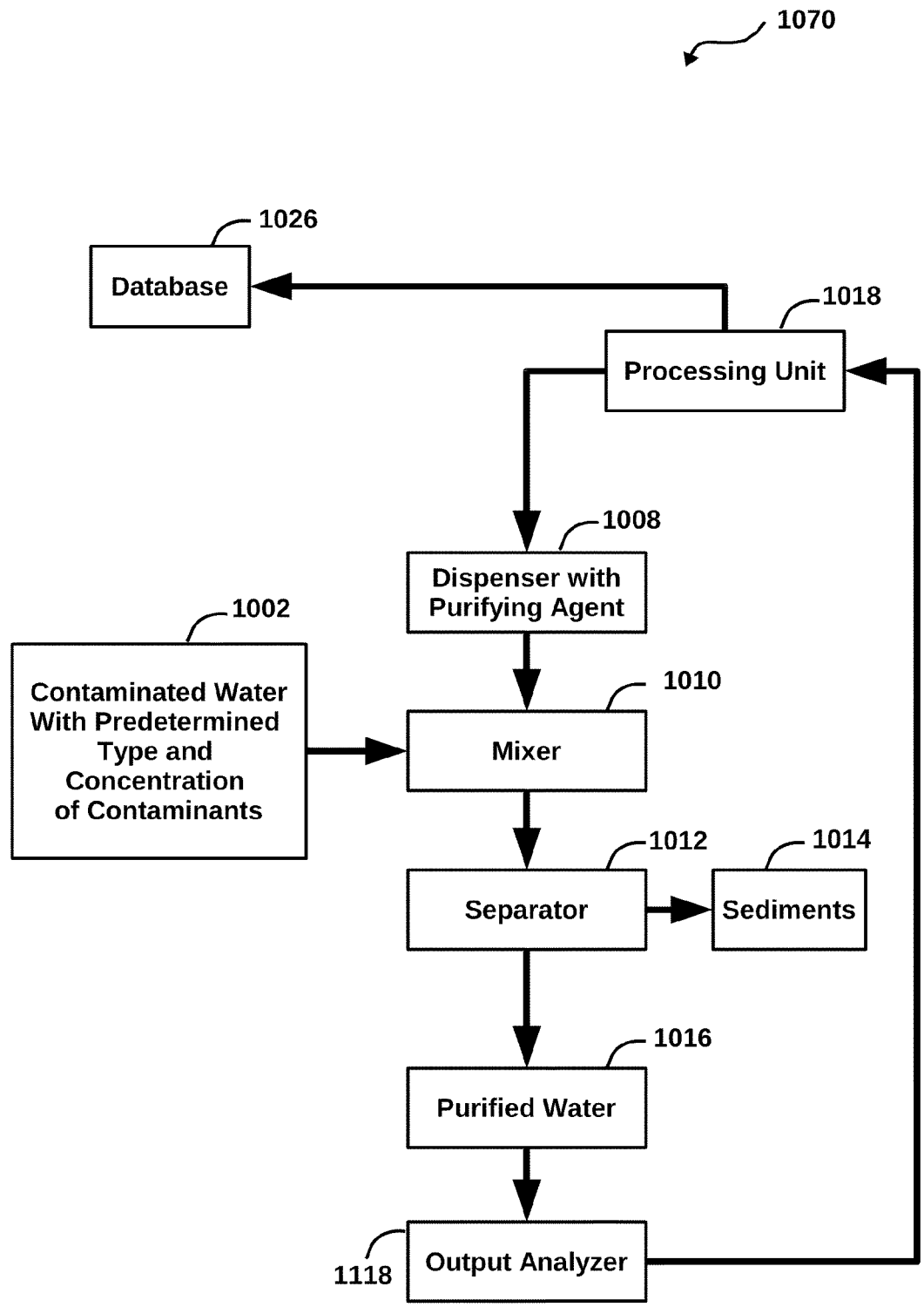
FIG. 5a illustrates a processing system for experimentally determining coefficients for approximating the logistic function.

Processing System for Experimentally Determining Coefficients for Approximating the Logistic Function FIG. 5a illustrates a processing system 1070 for experimentally determining the relationship between the concentration of the colloidal contaminants in the purified water $C_c$ and the concentration of the purifying agent $C_{pa}$ added to the contaminated water, and deriving corresponding coefficients for approximating said relationship using a suitable mathematical function such as logistic function, polynomial function, sigmoid function etc.

To determine values of the coefficients, a number of experiments are performed by dispensing various amounts, for example, progressively increasing amounts, of a selected purifying agent from the dispenser 1008 into the mixer 1010, mixing, in the mixer 1010, the dispensed purifying agent and the contaminated water having a predetermined type and concentration of the colloidal contaminants 1002, and measuring a resulting concentration of the colloidal contaminants in the purified water 1016 in an output analyzer 1118. Concentration and type of the colloidal contaminants 1002 is supplied to a Processing Unit 1018 having a processor and a computer readable storage medium having computer readable instructions stored thereon for execution by the processor. The Processing Unit 1018 also controls the dispenser 1008.

These experimental data, i.e. [$C_c$, $C_{pa}$] pairs, are processed in a Processing Unit 1018, using a suitable mathematical method, for example a non-linear regression, in particular, non-linear least square fit method, to determine values of the coefficients a, b, h, d, and f that allow for the best fit of the logistic function (1) to the experimental data. The determined values of the coefficients a, b, h, d, and f are stored in the database 1026 for fast retrieval when required. Other elements in FIGS. 5 and 5a are the same.

It is also contemplated that the relationship between the concentration of the colloidal contaminants in the purified water $C_c$ and the concentration of the purifying agent $C_{pa}$ added to the contaminated water can be stored in the database 1026 in a form of a table, and interpolation between data stored in the table may be performed.

Continuous Processing of Contaminated Water

Figure 7:
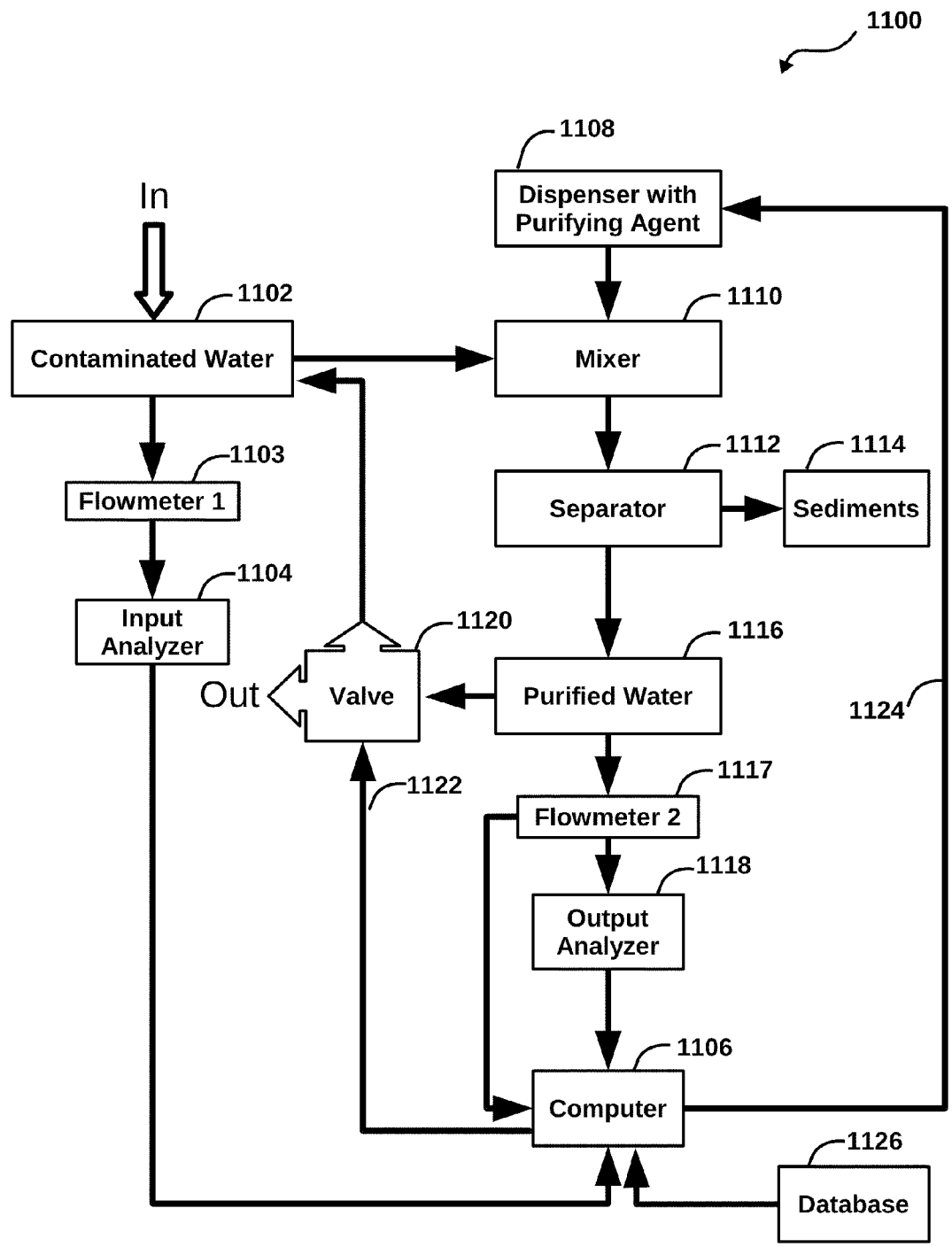
FIG. 7 illustrates a block diagram of the water purification system of an embodiment of the invention suitable for continuous processing of contaminated water.

FIG. 7 illustrates a second embodiment of the water purification system 1100 suitable for continuous processing of contaminated water. Elements of FIG. 7 similar to those shown on FIG. 5 are labeled by the same reference number incremented by 100.

Similarly to the batch processing, the relationship between the concentration of the colloidal contaminants in the purified water $C_c$ and the concentration of the purifying agent $C_{pa}$ can be approximated by various functions, such as logistic function, polynomial function, sigmoid function etc.

In the embodiment of the invention for continuous processing of contaminated water, the relationship between a concentration of the colloidal contaminants in the purified water $C_c$ and a concentration of the purifying agent $C_{pa}$ is represented by a logistic function, such as shown on FIG. 6, and expressed mathematically by the expression (1). The coefficients a, b, h, d, and f of the logistic function (1) are determined as described above with regard to the batch processing. The determined values of the coefficients are stored in the database 1126 for fast retrieval when required.

During purification of the contaminated water 1102 that flows continuously into the mixer 1110, concentration of colloidal contaminants is measured under control of the computer 1106 by using the flowmeter 1103 and the input analyzer 1104. In the preferred embodiment of the invention, the input analyzer 1104 is the fluid contamination analyzer described above and the flowmeter 1103 is a Paddlewheel Flowmeter, such as commercially available from the Cole-Parmer Instrument Company. Computer 1106 receives measurement signals from both the input analyzer 1104 and the flowmeter 1103, divides the amount of the colloidal contaminants, as measured by the analyzer 1104, by the total volume of water from which it was extracted, as determined from the flow rate measured by the flowmeter 1003, obtaining, as a result, the concentration of the colloidal contaminants in the contaminated water. This allows for on-the-fly remote monitoring of the concentration of the colloidal contaminants, which is both efficient and reliable. The frequency of the analysis is determined by the probable intervals of time in which significant changes of the concentration of the colloidal contaminants is expected, which in real life situations often varies from a few minutes to tens of minutes, depending on a particular application.

Provided the type of the contaminant or a combination of the contaminants in the contaminated water are known, and the concentration of the colloidal contaminants is determined as described above, the computer 1106 queries the database 1126 to retrieve coefficients a, b, h, d, and f that fully determine the logistic function (1) corresponding to the current combination of contaminants. Given the target concentration Ct, the computer 1106 computes from the fully determined logistic function an estimated optimal concentration of the purifying agent. The computer 1106 also computes an estimated optimal rate of dispensing of the purifying agent, which is a rate of dispensing that provides for the optimal concentration of the purifying agent in the contaminated water. This is accomplished by multiplying the estimated optimal concentration of the purifying agent and a rate of the contaminated water supply measured by the flow meter 1103. The estimated optimal rate is applied to dispensing the purifying agent 1108 into the mixer 1110 in the form of slurry. The mixture of the slurry and the contaminated water flows through the mixer for a predetermined mixing time relevant to the concentration of the colloidal contaminants to allow the purification process to be completed. The mixer is to provide thorough mixing between the purifying agent and the contaminated water in order to reduce the diffusion time of the purifying agent in the water. In the preferred embodiment of the invention, a helical static mixer, such as the Kenics Motionless Mixer from the Kenics Corporation, is used. The mixing time varies with a type of the purifying agent used and the type and the concentration of the colloidal contaminants. Typically, the mixing time is on the order of seconds, which is substantially faster than in the case of the batch processing disclosed above. As a result of the mixing, the colloidal contaminants are entrapped by the purifying agent forming a mixture of the purifying agent with the entrapped contaminants and purified water. The mixture is fed into the separator 1112 which is designed to effectively remove the purifying agent with the entrapped contaminants from the mixture, returning the contaminated water to its original clean condition. In the preferred embodiment of the invention, the separator is a hydrocyclone, such as one of those commercially available from ChemIndustrial Systems Inc. The solid sediments of the purifying agent with the entrapped contaminants are repelled to the sediments tank 1114, whereas purified water 1116 is analyzed by the output analyzer 1118 to determine whether the purification process has succeeded in lowering the concentration of the colloidal contaminants in the contaminated water below the target concentration defined by the regulatory authorities. The output analyzer 1118 is similar to the input analyzer 1104 but has much higher sensitivity, because it needs to detect much lower levels of the colloidal contaminants in the purified water, higher precision, faster response and finer adjustment compared with the input analyzer 1104. The flowmeter 1117 is similar to the flowmeter 1103. Readings from the flowmeter 1117 and the output analyzer 1118 are processed by the computer 1106 in the same fashion as readings from the flowmeter 1103 and the input analyzer 1104 as described above. The concentration of the colloidal contaminants in the purified water is compared with the target concentration. If the concentration of the colloidal contaminants in the purified water 1116 is lower than the target concentration, current rate of dispensing of the purifying agent remains unchanged and the computer 1106 controls valve 1120 to deliver the purified water further for consumption. Otherwise, the computer 1106 controls the dispenser 1108 to increase the rate of dispensing of the purifying agent to fine tune the purification process into the compliance with the regulations, i.e. until concentration of the colloidal contaminants in the purified water 1116 is lower than the target concentration.

A control algorithm used by the computer closes a loop (1108 to 1106 with feedback 1124) and ensures that the target concentration of colloidal contaminants in the purified water is maintained continuously and automatically.

Various control algorithms can be used by the computer to control the rate of dispensing, such as a Proportional-Integral-Derivative (PID), adaptive control, artificial intelligence, neural networks etc.

Before the purified water 1116 becomes compliant with the regulations, it is redirected back to the contaminated water 1102 for reprocessing.

In yet another embodiment of the present invention, the amount of increase in the rate of dispensing of the purifying agent is determined as follows.

Water purification process of the embodiments of the present invention is based on the metathetical reaction and therefore is a predictable, "mass balanced" chemical process. For this reason, the rate of dispensing of the purifying agent is exercised by assuming a known constant ratio of measured concentration of the colloidal contaminants in the contaminated water, (mass per unit volume) to the required concentration of the purifying agent (mass per unit volume) as follows:

$$\text{"Purifying agent"} = \text{"Loading Factor"} * \text{"Contaminant"} \quad (2)$$

In this relationship, the "Loading Factor" calibrates the performance of the purification process. It is defined in each specific purification procedure as the ratio of the mass of the optimized form of purifying agent needed to entrap a standard amount of the target contaminant. The "Loading Factor" is stored in a database as a part of a look-up table and accessed by human or by a computing device. If concentration of the colloidal contaminants in the purified water 1116 is higher than the target concentration, the concentration of the colloidal contaminants is substituted into the "Contaminant" part of the expression (2) to determine the "Purifying agent" part which represents the amount of increase in the rate of dispensing of the purifying agent.

If the concentration of the colloidal contaminants in the contaminated water 1102 changes, e.g. because of an emergency discharge into the source of the contaminated water, the input analyzer 1104 will provide new readings to the computer 1106, which will establish a new rate of dispensing of the purifying agent 1108. As a result of the new rate of dispensing, the concentration of the colloidal contaminants in the purified water is changed. It causes the output analyzer 1118 to provide new readings to the computer 1106, which will determine whether the purification process has succeeded in getting the concentration of the colloidal contaminants in the purified water below the target concentration defined by the regulatory authorities. If necessary, the computer 1106 will control the dispenser 1108 to adjust the rate of dispensing of the purifying agent to fine tune the purification process into the compliance with the regulations. As a result, the purification system of FIG. 7 automatically adapts to the new concentration of the colloidal contaminants, without the need for human intervention.

The mixer and the separator may not always be clearly divided components. In one case, the mixer provides larger part of the mixing but additional mixing may continue occur in the separator. In another case, the mixer and the separator may be designed as one integrated component/chamber performing mixing and separation sequentially. There are also a number of important auxiliary components such as pumps, check valves, feed control valves, pressure gauges, and flow rate meters etc. needed. They help to maintain the required specific feed pressures and flow rates for both the contaminated water and the purifying agent. Various types of other mixers, such as an eductor or a certain types of fluidized bed can also be used instead of the helical static mixer. Other types of separators, such as a filter with or without pressure, a centrifuge, or a vortex separator can also be used instead of the hydrocyclone.

For certain applications, such as purification of water for industrial purposes and non-drinking water, a simpler design of the input analyzers 1004, 1104 and the output analyzer 1118 may provide more compact, cheaper and still tolerably efficient alternative to the input and output analyzers based on the initially described ellipsoidal collection system.

Alternative Design of the Fluid Contamination Analyzer

Figure 8:
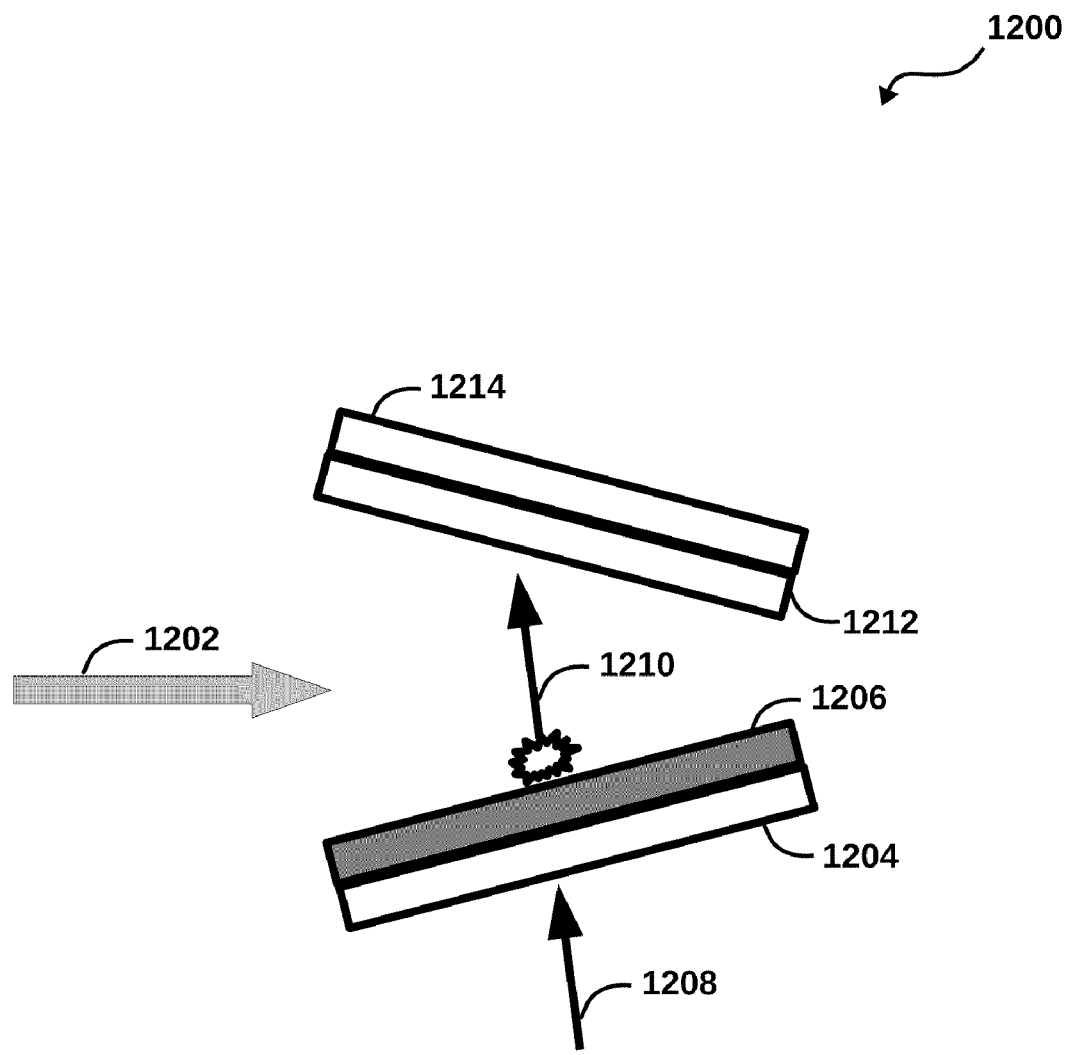
FIG. 8 illustrates a block diagram of a simplified design of the fluid contamination analyzer for use in the water purification systems of FIGS. 5 and 7.

An alternative, simplified design of the input analyzers 1004, 1104 and the output analyzer 1118 represents a tolerably efficient geometric compromise that can be reached between collection of a sample from the contaminated water flow and collection of emitted radiation when the analyte is collected onto the surface of substrate in a wedge configuration to the detector, as shown in FIG. 8. The analyte is concentrated by passing contaminated water 1202 through a solid substrate 1204, which is chemically treated to make analytes adhere to its surface as disclosed in detail in U.S. Pat. No. 5,512,491 and Canadian Patent No. 2093676. The sample is illuminated with a monochromatic source 1208, such as a laser or a photodiode, at a wavelength set to excite the analyte to a fluorescent state. The half of the total emission emerging from the opposite surface of the collected analyte 1206 to its illumination then passes through the contaminated water, an optical filter 1212 to remove any remnant of the excitation light. It immediately falls onto the active area of the detector 1214. Performance of the detector 1214 is improved geometrically by maximizing the aperture through increasing the fraction of emitted photons striking the detector. This intensity is further increased from less than half of the initial emission to considerably more than half by making the substrate 1204 reflective to the emission wavelength and making the sample from the contaminated water flow sufficiently thin, typically 1~2 mm. Further increase in the detection performance is achieved by operating the detector 1214 in the avalanche photodiode mode. In the simple photoconductive mode, the detector 1214 is operated under reverse bias of an externally applied DC level. The photocurrent is then linearly proportional to the illuminance but this mode optimizes the response time at the expense of increased noise. In the avalanche photodiode mode, the detector 1214 is operated with much higher reverse bias. This allows each photo-generated carrier to be multiplied by avalanche breakdown, resulting in internal gain within the photodiode. This provides improvement in both absolute signal strength and in the relative signal to noise ratio. Together these conditions provide a large net increase of the effective responsiveness of the detector 1214.

Although the method and system of the embodiments of the invention have been described with regard to water purification, it is contemplated that similar methods and system can be used for purifying other aqueous fluids.

Although particular embodiments of the invention have been described in detail, it can be appreciated that alternatives, such as those mentioned above and numerous other changes, variations, and adaptations may be made without departing from the scope of the invention as defined in the following claims.

What is claimed is:

1. A system for purifying an aqueous contaminated fluid from colloidal contaminant using a purifying agent, the system comprising:
   (a) an input analyzer, measuring a concentration of the colloidal contaminant in the aqueous contaminated fluid, the input analyzer comprising:
      (a1) a sample cell, comprising:
         (i) a trapping medium for entrapping the colloidal contaminant from the aqueous contaminated fluid flowing through the trapping medium; the trapping medium being made of the same material as the purifying agent the purifying agent possessing metathetical properties;
         (ii) the trapping medium having an outer surface and an inner surface; the trapping medium being translucent and having an essentially closed form defined by the outer surface, with a cavity formed inside thereof defined by the inner surface;
         (iii) an outer structural support surface and an inner structural support surface formed on or adjacent to the outer surface and the inner surface respectively; and
         (iv) a radiation source illuminating the trapping medium with excitation radiation to cause the entrapped colloidal contaminant to generate a secondary radiation indicative of identity of the colloidal contaminant, or the identity and the concentration of the colloidal contaminant the radiation source being placed inside the cavity to illuminate the trapping medium from inside thereof outwards;
   (b) a mixer, mixing the purifying agent and the aqueous contaminated fluid, resulting in a mixture of the purifying agent with the entrapped colloidal contaminant and aqueous purified fluid;
   (c) a processor and a computer readable storage medium having computer readable instructions stored thereon for execution by the processor, for:
      (c1) retrieving a relationship, stored in the computer readable medium, between the concentration of the colloidal contaminant in the aqueous purified fluid and concentration of the purifying agent supplied to the aqueous contaminated fluid;
      (c2) retrieving a target concentration of the colloidal contaminant in the aqueous purified fluid stored in the computer readable storage medium;
      (c3) determining an estimated optimal concentration of the purifying agent in the aqueous contaminated fluid required for achieving the target concentration of the colloidal contaminant in the aqueous purified fluid based on said relationship and the target concentration;
      (c4) controlling dispensing of the purifying agent into the mixer in an amount required to achieve the estimated optimal concentration of the purifying agent in the aqueous contaminated fluid; and
   (d) a separator, removing the purifying agent with the entrapped colloidal contaminant from the mixture to obtain the aqueous purified fluid.

2. The system of claim 1, wherein the computer readable instructions (c1) for retrieving the relationship comprise coefficients of a function approximating said relationship.

3. The system of claim 2, further comprising a processing unit, comprising a processor and a computer readable storage medium having computer readable instructions stored thereon for execution by the processor, for:
   prior to the purifying the aqueous contaminated fluid, determining the coefficients from a number of experiments, including mixing various concentrations of the purifying agent and the aqueous contaminated fluid having a predetermined type and concentration of the colloidal contaminant, and measuring a resulting concentration of the colloidal contaminant in the aqueous purified fluid, thereby obtaining said relationship.

4. The system of claim 1, wherein said relationship is a logistic function.

5. The system of claim 2, wherein the input analyzer further comprises:
   (f) a detector for detecting the secondary radiation; and
   (g) a reflective shell at least partly encompassing the sample cell and the detector, the shell having a shape defining two focal points so that radiation generated at one of the focal points is substantially reflected by the reflective shell to the other focal point, the sample cell being disposed at or in close proximity to one of the focal points, and the detector being disposed at or in close proximity to the other focal point to receive the secondary radiation generated by the entrapped colloidal contaminant.

6. The system of claim 1, wherein the trapping medium comprises a three-dimensional matrix of micro-porous adsorbent support material, whose surface has been chemically reconstructed with a surface reconstruction reagent to bear active, hydrated hydroxyl groups, which provide irreversible binding sites, providing absorption and entrapment of colloids and entrained analytes by immobilizing said colloids on said surface through the release of hydronium/hydrogen ions from the hydroxyl groups.

7. The system of claim 1, wherein the computer readable instructions for controlling dispensing further comprise computer readable instructions stored in the computer readable storage medium for execution by the processor, for determining a rate of dispensing of the purifying agent required for continuously maintaining the estimated concentration of the purifying agent in the aqueous contaminated fluid.

8. The system of claim 7, further comprising:
   an output analyzer for measuring concentration of the colloidal contaminant in the aqueous purified fluid, the trapping medium of the output analyzer being made of the same material as the purifying agent; and
   computer readable instructions stored in the computer readable storage medium for execution by the processor for adjusting the rate of dispensing of the purifying agent in response to a signal from the output analyzer until the concentration of the colloidal contaminant in the aqueous purified fluid is equal to or below the target concentration.

9. The system of claim 1, further comprising an output analyzer for measuring an output concentration of the colloidal contaminant in the aqueous purified fluid, the trapping medium of the output analyzer being made of the same material as the purifying agent.

10. The system of claim 9, wherein the output analyzer comprises:
   (a1) a sample cell, comprising:
      (i) the trapping medium having an outer surface and an inner surface; the trapping medium being translucent and having an essentially closed form defined by the outer surface, with a cavity formed inside thereof defined by the inner surface;
      (ii) an outer structural support surface and an inner structural support surface formed on or adjacent to the outer surface and the inner surface respectively; and
      (iii) a radiation source illuminating the trapping medium with excitation radiation to cause the entrapped colloidal contaminant to generate a secondary radiation indicative of identities of the entrapped colloidal contaminant, or an identity and concentration of the entrapped colloidal contaminant; the radiation source being placed inside the cavity to illuminate the trapping medium from inside thereof outwards.

11. The system of claim 10, wherein the output analyzer further comprises:
   (f) a detector for detecting the secondary radiation; and
   (g) a reflective shell at least partly encompassing the sample cell and the detector, the shell having a shape defining two focal points so that radiation generated at one of the focal points is substantially reflected by the reflective shell to the other focal point, the sample cell being disposed at or in close proximity to one of the focal points, and the detector being disposed at or in close proximity to the other focal point to receive the secondary radiation generated by the entrapped colloidal contaminant.

12. The system of claim 1, wherein the separator is one of the following: hydrocyclone, spiral separator, filter based separation system, clarifier, dissolved air flotation system, centrifuge.

13. The system of claim 1, wherein the mixer is one of the following: a helical static mixer, vortex mixer, mixing eductor, Jacobi-Tarbox eductor, tank eductor, propeller blade mixer, fluidized bed, ultrasonic mixer, rotary mixer, high shear mixer, tumble drum.

14. A method of purifying an aqueous contaminated fluid from colloidal contaminant using a purifying agent, the method comprising:
   (a) employing an input analyzer, measuring concentration of the colloidal contaminant in the aqueous contaminated fluid; the input analyzer comprising:
   a sample cell, comprising:
      (i) a trapping medium for entrapping the colloidal contaminant from the contaminated aqueous fluid flowing through the trapping medium, the trapping medium having an outer surface and an inner surface; trapping medium made of the same materials as the purifying agent the purifying agent possessing metathetical properties;
      (ii) the trapping medium being translucent and having an essentially closed form defined by the outer surface, with a cavity formed inside thereof defined by the inner surface;
      (iii) an outer structural support surface and an inner structural support surface being formed on or adjacent to the outer surface and the inner surface respectively; and
      (iv) a radiation source illuminating the trapping medium with excitation radiation to cause the entrapped contaminant to generate a secondary radiation indicative of identity of the contaminant, or the identity and the concentration of the contaminant the radiation source being placed inside the cavity to illuminate the trapping medium from inside thereof outwards;
   (b) retrieving a relationship between the concentration of the colloidal contaminant in the aqueous purified fluid and concentration of the purifying agent aqueous purified fluid;
   (c) selecting a target concentration of the colloidal contaminant in the aqueous purified fluid;
   (d) determining an estimated optimal concentration of the purifying agent in the aqueous contaminated fluid required for achieving the target concentration of the colloidal contaminant in the aqueous purified fluid based on said relationship and the target concentration;
   (e) controlling dispensing of the purifying agent in an amount required to achieve the estimated optimal concentration of the purifying agent in the aqueous contaminated fluid;
   (f) mixing the purifying agent dispensed in the step (e) and the aqueous contaminated fluid, resulting in a mixture of the purifying agent with the entrapped colloidal contaminant and the aqueous purified fluid; and
   (g) separating the purifying agent with the entrapped colloidal contaminant from the mixture to obtain the aqueous purified fluid.

15. The method of claim 14, wherein the retrieving the relationship comprises retrieving coefficients of a function approximating said relationship.

16. The method of claim 15, further comprising determining the coefficients, comprising performing a number of experiments, prior to the purifying the aqueous contaminated fluid, by mixing various concentrations of the purifying agent and the aqueous contaminated fluid having the predetermined type and concentration of the colloidal contaminant, and measuring a resulting concentration of the colloidal contaminant in the aqueous purified fluid, thereby obtaining said relationship.

17. The method of claim 15, wherein said relationship is a logistic function.

18. The method of claim 14, further comprising determining a rate of dispensing of the purifying agent required to continuously maintain the estimated concentration of the purifying agent in the aqueous contaminated fluid.

19. The method of claim 18, further comprising:
   measuring concentration of the colloidal contaminant in the aqueous purified fluid, including directing a flow of the aqueous purified fluid through a trapping medium made of the same material as the purifying agent; and
   adjusting the rate of dispensing of the purifying agent in response to a signal indicative of the measured concentration of the colloidal contaminant in the aqueous purified fluid until the concentration of the colloidal contaminant in the aqueous purified fluid is equal to or below the target concentration.

20. The system of claim 1, wherein the radiation source comprises a diffuser for dispersing the excitation radiation substantially in a $4\pi$ steradian angle.

* * * * *

UNITED STATES PATENT AND TRADEMARK OFFICE
CERTIFICATE OF CORRECTION

| | | |
|---|---|---|
| PATENT NO. | : 8,338,186 B2 | Page 1 of 1 |
| APPLICATION NO. | : 12/790924 | |
| DATED | : December 25, 2012 | |
| INVENTOR(S) | : Bryan R. Hollebone et al. | |

It is certified that error appears in the above-identified patent and that said Letters Patent is hereby corrected as shown below:

Column 21, line 28, "agent the" should read --agent, the--.

Column 21, line 44, "contaminant the" should read --contaminant, the--.

Column 23, line 46, "from colloidal" should read --from a colloidal--.

Column 23, line 48, "measuring concentration" should read --measuring a concentration--.

Column 23, line 57, "agent the" should read --agent; the--.

Column 24, line 5, "contaminant the" should read --contaminant, the--.

Signed and Sealed this
Twenty-ninth Day of January, 2013

David J. Kappos
*Director of the United States Patent and Trademark Office*